(12) United States Patent
Bruder et al.

(10) Patent No.: US 8,615,122 B2
(45) Date of Patent: Dec. 24, 2013

(54) METHOD FOR REDUCTION OF THE RADIATION DOSE USED WITHIN THE FRAMEWORK OF AN X-RAY IMAGING EXAMINATION AND CT SYSTEM

(75) Inventors: Herbert Bruder, Höchstadt (DE); Thomas Flohr, Uehlfeld (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 111 days.

(21) Appl. No.: 13/273,504

(22) Filed: Oct. 14, 2011

(65) Prior Publication Data

US 2012/0121148 A1    May 17, 2012

(30) Foreign Application Priority Data

Nov. 16, 2010   (DE) .......................... 10 2010 043 975

(51) Int. Cl.
  *G06K 9/00* (2006.01)
  *A61B 6/00* (2006.01)
(52) U.S. Cl.
  USPC .................................... 382/131; 378/4; 378/8
(58) Field of Classification Search
  USPC ......... 382/128, 129, 130, 131, 132, 133, 134; 378/4, 8, 21–27, 101, 901; 600/407, 600/410, 411, 425, 427, 428; 128/920, 922
  See application file for complete search history.

(56) References Cited

U.S. PATENT DOCUMENTS

| | | | |
|---|---|---|---|
| 5,602,934 A * | 2/1997 | Li et al. ........................ | 382/128 |
| 5,848,117 A * | 12/1998 | Urchuk et al. .................. | 378/19 |
| 6,574,304 B1 * | 6/2003 | Hsieh et al. ..................... | 378/62 |
| 7,499,576 B2 * | 3/2009 | Setala .......................... | 382/128 |
| 7,864,916 B2 * | 1/2011 | Akino ............................. | 378/4 |
| 2004/0228444 A1 | 11/2004 | Bohm et al. | |
| 2005/0190984 A1 | 9/2005 | Fischer et al. | |
| 2007/0040831 A1 | 2/2007 | Flohr et al. | |
| 2011/0052030 A1 * | 3/2011 | Bruder et al. ................. | 382/131 |

FOREIGN PATENT DOCUMENTS

| | | |
|---|---|---|
| DE | 10309166 A1 | 9/2004 |
| DE | 102004008979 B4 | 12/2006 |
| DE | 102005038940 B4 | 8/2007 |
| DE | 102009014724 A1 | 10/2010 |
| DE | 10-2009-039987 | 3/2011 |

OTHER PUBLICATIONS

Pietro Perona et al.; "Scale-Space and Edge Detection Using Anisotropic Diffusion", IEEE Transactions on Pattern Analysis and Machine Intelligence, vol. 12, No. 7, Jul. 1990, pp. 629 to 639; Others; 1990.

(Continued)

*Primary Examiner* — Abolfazl Tabatabai
(74) *Attorney, Agent, or Firm* — Harness, Dickey & Pierce, P.L.C.

(57) ABSTRACT

A method and an X-ray system are disclosed for reduction of the radiation dose used within the framework of an imaging X-ray examination. In at least one embodiment, for each pixel of a recorded image, structure information of a structure which may be present at a distance around the examined pixel is determined and a direction-dependent lowpass filter is applied to the pixel examined in each case, which filter's spatial coverage is less than the distance and which takes into account the morphological information of a structure which may be present with a direction-dependent weighting of the lowpass filter.

20 Claims, 4 Drawing Sheets

(56) References Cited

OTHER PUBLICATIONS

J. Weickert, "Anisotropic Diffusion in Image Processing", Teubner-Verlag, Stuttgart, Germany, 1998, pp. 95-105; Book.

Fernandez G. et al. Nonlinear Filters on 3D CT Imaging—Bilateral Filter and Mean Shift Filter Computer Vision Winter Workshop, pp. 21-26, O. Drbohlav (ed.), Valtice, Czech Republic., 2003 Proceedings of 8th CVWW, Valtice, Czech Republic, pp. 21-26, Feb. 2003.; Others; 2003.

Per-Erik Danielsson et al. Efficient Detection of Second-Degree Variations in 2D and 3D Images Journal of Visual Communication and Image Representation 12, pp. 255-305 (2001); Others.

Wilhelm Burger et al. Kapitel 10: "Morphologische Filter" Seiten 169-194, aus "Digitale Bildverarbeitung Eine Einführung mit Java und ImageJ" 1. Auflage mit 529 Seiten, 245 Abbildungen und 16 Tabellen eXamen.press • ISBN 3-540-21465-8 © Springer-Verlag Berlin Heidelberg, May 2005; Book; 2005.

German Priority Application No. DE 10 2010 043 975.4 dated Nov. 16, 2010 (not yet published).

\* cited by examiner

METHOD FOR REDUCTION OF THE RADIATION DOSE USED WITHIN THE FRAMEWORK OF AN X-RAY IMAGING EXAMINATION AND CT SYSTEM

PRIORITY STATEMENT

The present application hereby claims priority under 35 U.S.C. §119 on German patent application number DE 10 2010 043 975.4 filed Nov. 16, 2010, the entire contents of which are hereby incorporated herein by reference.

FIELD

At least one embodiment of the invention generally relates to a method and/or a CT system for reduction of the radiation dose used within the framework of an X-ray imaging examination, especially a CT examination, whereby a patient is scanned or X-rayed, a projection or tomographic image with a plurality of pixels is generated and the image is filtered to improve the image quality.

BACKGROUND

Essentially, known noise reduction algorithms can be traced back to two different and in each case separately used principles, namely diffusion filters on one hand and morphological or edge-preserving filters on the other hand.

Diffusion filters look at the difference between pixel values in relation to statistical uncertainty. As well as the simple diffusion filters, bilateral filters or regularizers used for iterative reconstructions in accordance with patent application DE 10 2009 039 987.9-35 also belong to this class.

SUMMARY

The inventors have discovered that a problem with this filter principle is the fact that differences from neighboring values are considered individually. If such filters are designed so that they are edge-preserving, the danger also increases of obtaining or even emphasizing statistical outliers. This also includes fraying of edges which are caused by noise. To this extent the maximum achievable noise reduction with simultaneous edge preservation is limited.

At least one embodiment of the invention is thus directed to finding an improved method of reducing the radiation dose used within the framework of an X-ray imaging examination, especially in a CT examination, through an improved image filtering technique.

Advantageous developments of embodiments of the invention are the subject matter of subordinate claims.

The inventors have recognized the following: Morphological or structural filters mostly analyze the structural characteristics of the environment and especially detect the orientation of edges. This can be done with the aid of suitable operators, as are known from the prior art. As an alternative this can also be done by calculating direction-dependent variance values, as is shown in publications DE 10 2004 008 979 B4 and DE 10 2005 038 940 B4, the entire contents of each of which are hereby incorporated herein by reference. Subsequently locally adaptive filters are used which are adapted in the optimum manner in accordance with the orientation determined.

Since reliable analysis of the morphology requires a certain spatial coverage of the operators used, there is the danger of smaller structures being adversely affected during filtering. With a range that is too short the analysis is uncertain in the sense that statistical effects influence the computed orientation and thus the filtering undertaken does not match the actual orientation. To this extent, in accordance with at least one embodiment of the invention, there should be a compromise in morphological filtering between the reliability of the orientation determination and the damage to small structures for which information from intelligent edge-preserving image filters which is either applied directly to image data for quality improvement or is used within the framework of iterative methods as a regularization step, can be used.

The result of the filtering and thus the potential for noise and dose reduction can thus be improved by both principles being skillfully combined. In this way it is possible to apply short-range and pixel value difference-dependent filters and orientation analyses to greater length scales simultaneously. A concrete example of this is described in detail further on in this document.

At least one embodiment of the invention thus shows a method and an X-ray system, especially a CT system, wherein for reduction of the radiation dose used within the framework of an X-ray imaging examination, for each pixel of a recorded image, structure information of a structure which may be present at a predetermined distance around the examined pixel is determined and a direction-dependent lowpass filter is applied to the respective pixel examined, which filter has a smaller spatial coverage than the predetermined distance and takes into account the morphological information of a structure that may be present with a direction-dependent weighting of the lowpass filter.

In accordance with this basic concept and the concrete example of an embodiment described further on in the document, the inventors propose to improve the known method for reduction of the radiation dose used within the framework of an imaging X-ray examination, especially of a CT examination, with the following method steps:

scanning or fluoroscopy of the patient by X-raying,
generation of a projectional or tomographic image with a plurality of pixels, and
filtering of the image for improving the image quality.

Inventively, at least one embodiment of this method is improved by:

structure information, including directional information of any structure which may be found, being sought for each pixel in a surrounding circle with a first radius around the examined pixel, and
a direction-dependent lowpass filter being applied to the examined pixel, with on the one hand its spatial coverage being smaller than the first radius and on the other hand the direction information of any structure which may be found being taken into account for a direction-dependent weighting of the lowpass filter.

In addition to embodiments of the inventive method, the inventors also disclose, in at least one embodiment, a computer system for processing X-ray and/or CT image datasets which comprises a memory and computer programs stored therein, wherein at least one computer program is to be stored and is to be executed during operation, and which performs a method with the following method steps:

receipt of X-ray or CT image datasets with a plurality of pixels,
for each pixel structure information, including direction information of any structure which may be found, is searched for in a circular area with a first radius around the examined pixel,
a direction-dependent lowpass filter is applied to the pixel under examination, wherein on the one hand its spatial coverage is less than the first radius and on the other hand the direction information of a structure which may possibly be found is taken into account for a direction-dependent weighting of the lowpass filter.

This inventive computer system of at least one embodiment can also include at least one computer program which executes the previously described method variants during operation.

It is explicitly noted that embodiments of the computer system described above can be operated either as a standalone system or in a computer network, as well as directly connected to a CT system or C-arm system.

BRIEF DESCRIPTION OF THE DRAWINGS

The invention will be explained in greater detail below with reference to an example embodiment with the aid of the figures, with only those features being presented that are necessary for understanding the invention. The following reference characters are used: C1: CT system; C2: first X-ray tube; C3: first detector; C4: second X-ray tube; C5: second detector; C6: gantry housing/drive system; C7: C-arm; C8: patient couch; C9: system axis; C10: regulation and control unit; P: patient; $Prg_1$-$Prg_n$: computer programs; 1.1: graph of an H function for linear lowpass filtering; 1.2: graph of an H function for edge-preserving smoothing; 1.3: graph of an H function for edge-preserving smoothing with steepening of the edge for high CNR values; 2: graph of the correction factor $h(v_{p,q})$; 3.1: unfiltered CT image of a patient; 3.2: CT image with filtering according to the prior art; 3.3: CT image with inventive filtering.

The individual figures are as follows.

DETAILED DESCRIPTION OF THE EXAMPLE EMBODIMENTS

Figure 1:
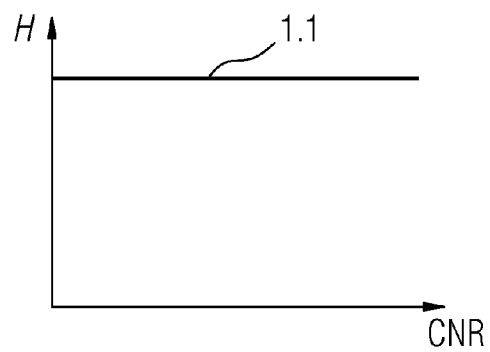
FIG. 1 shows the graph of an H function for linear lowpass filtering.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The invention will be illustrated with reference to the example embodiment below of an inventive expansion of a diffusion filter by additional morphological, i.e. structural, information.

Diffusion filters can be implemented by the iterative application of local filter steps. A filter step for the pixel value V(p) at the position p generally appears there as follows, $$V'(p) = V(p) + \alpha \sum_q g_{q,p} \cdot (V(q) - V(p)) \cdot H\left(\frac{|V(q) - V(p)|}{\sigma}\right). \quad (1)$$

In this case q indexes the neighboring pixels of p. $g_{q,p}$ defines the filter coefficients in the position space, e.g. with coefficients that are inversely proportional to the distance of the pixel q from p. $\alpha$ represents a suitable number that the person skilled in the art selects so that the convergence in the iteration of equation (1) is ensured. The influence function H defines the strength of the filtering depending on the local contrast-to-noise ratio (CNR), $|V(q)-V(p)|/\sigma$. $\sigma$ can be determined in different ways. One option of estimating $\sigma$ is the averaging of $v_{p,min}$ over the neighborhood of the considered pixel or even, i.e.

$$\sigma := \sqrt{\frac{1}{N_p} \sum_{p'} v_{p',min}},$$

where p' passes through either a neighborhood of p in order to compute a pixel-dependent noise value $\sigma_p$ or via all pixels, in order to obtain a global noise value $\sigma$.

Figure 2:
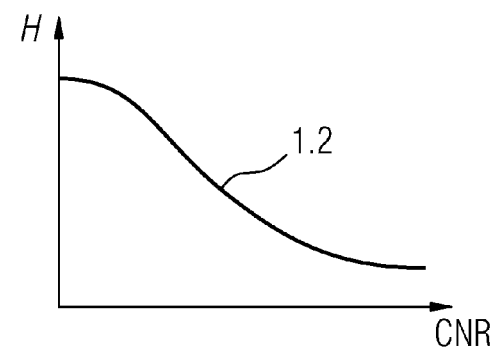
FIG. 2 shows the graph of an H function for edge-preserving smoothing.
Figure 3:
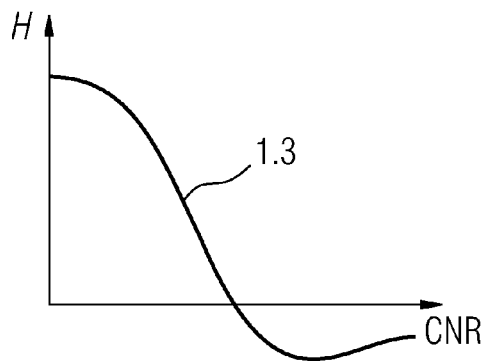
FIG. 3 shows the graph of an H function for edge-preserving smoothing with steepening of the edge for high CNR values.

FIGS. 1 through 3 show graphs of three different H functions which lead to the following characteristics of filtering, wherein the influence value H is shown on the ordinate versus the local CNR on the abscissa. FIG. 1 shows the graph 1.1 of the H function which leads to linear lowpass filtering, FIG. 2 shows the graph 1.2 of the H function for edge-preserving smoothing and FIG. 3 shows the graph 1.3 of the H function for edge-preserving smoothing with a steepening of the edge for high CNR values.

For a filter in accordance with FIG. 3 in particular, individual pixels of which the CNR to the neighborhood is large, stand as outliers or are even enhanced in contrast. This occurs especially if the zero crossing of the H function is selected too small, i.e. lies in the vicinity of 1 for example. On the other hand with this filter, if the H function drops off too slowly, the selectivity between noise and edges is poor so that the sharpness of edges is reduced by the filtering. Since all differences of the pixel values from the central pixel are evaluated separately, the filtering also only functions in the optimum manner if the noise is white, i.e. neighboring pixels are uncorrelated in terms of their statistics.

The problems can be reduced by an embodiment of the inventive method described. In accordance with the embodiment of the method, before the filter step, in addition to determining the local noise, an analysis of the morphology of the further pixel environment is carried out. This can be done with the aid of determining one-dimensional variance values, as is described for example in the already cited publications DE 10 2004 008 979 B4 and DE 10 2005 038 940 B4, the entire contents of each of which is hereby incorporated herein by reference. The value $v_{p,q}$ then describes the variance in the direction of the connecting line of the pixels q and p. The decisive factor in this case is that the range for investigating the morphology is selected so that it is greater than the noise kernel size or the range of the autocorrelation function described there. If the noise is not white, neighboring pixels are namely correlated in relation to their statistical fluctuations.

The morphological information can advantageously be used if for example the argument of the influence function is replaced by an effective CNR value, $$H\left(\frac{|V(q) - V(p)|}{\sigma}\right) \to H\left(\frac{|V(q) - V(p)|}{\sigma} \cdot h(v_{p,q})\right). \quad (2)$$

The correction factor $h(v_{p,q})$ has the characteristic of being less than 1 for small variance values, i.e. specifies a smaller CNR and thus in accordance with FIG. 2 or 3, leads to a stronger smoothing, conversely however for large variance values is greater than 1, i.e. leads to a smaller smoothing or even to a greater steepening. The evaluation "small" or "large" can be undertaken either by comparing $v_{p,q}$ with the local noise amplitude $\sigma$, or by comparing the variances of all directions. In the second case the minimum and maximum variances are defined first, $$v_{p,min} = \min\{v_{p,q} | q \in \text{neighborhood of } p\} \text{ and} \quad (3a)$$

$$v_{p,max} = \max\{v_{p,q} | q \in \text{neighborhood of } p\}. \quad (3b)$$

Figure 4:
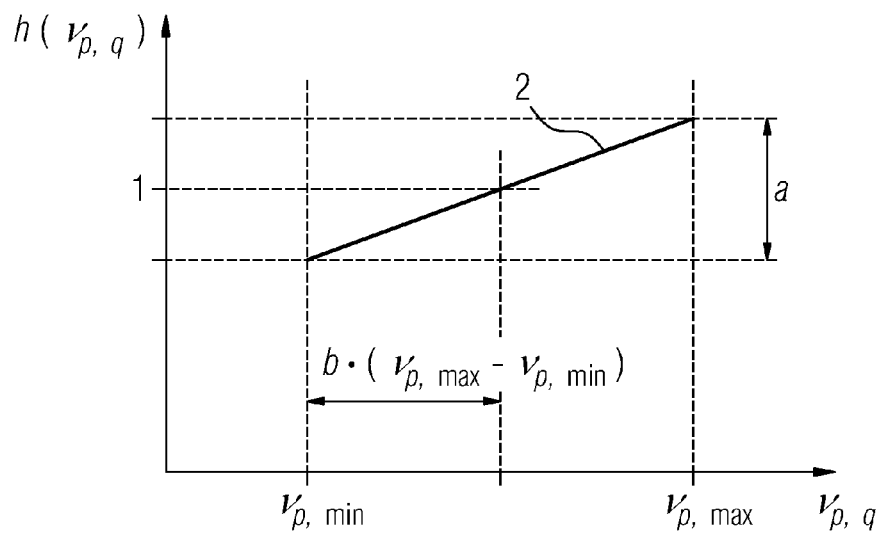
FIG. 4 shows the graph of the correction factor $h(v_{p,q})$.

A possible function, of which the graph 2 is shown in FIG. 4, can then be defined for example with the following formula:

$$h(v_{p,q}) = 1 + \alpha \cdot \left(\frac{v_{p,q} - v_{p,min}}{v_{p,max} - v_{p,min}} - b\right). \quad (4)$$

The parameter a here determines the strength of the adaptation, while b defines the position of the neutral point.

However other functions are also conceivable with the required elementary characteristics. A further improvement is an adaptation to the local measure of isotropy, $$\eta_p = \frac{2 v_{p,min}}{v_{p,max} + v_{p,min}} \in ]0, 1], \quad (5)$$

in the form of a modified correction factor, $$h(v_{p,q}) = 1 + \alpha \cdot (1 - \eta_p) \cdot \left(\frac{v_{p,q} - v_{p,min}}{v_{p,max} - v_{p,min}} - b\right). \quad (6)$$

This weakens the correction mechanism in the event of an isotropic environment.

An alternate option of an embodiment of the inventive use of the morphological information is represented by convoluting two different influence functions $H_1$ and $H_2$ which take account in each case of the CNR on different length scales:

$$H\left(\frac{|V(q) - V(p)|}{\sigma}\right) \to \quad (7)$$

-continued $$(1 - c_{p,q}) \cdot H_1\left(\frac{|V(q) - V(p)|}{\sigma}\right) + c_{p,q} \cdot H_2\left(\frac{|V(q) - V(p)|}{\sigma}\right).$$

A possible weighting function can appear as follows, $$c_{p,q} = \min\left\{\underbrace{a \cdot (1 - \eta_p)}_{(I)} \cdot \underbrace{\left(1 + \frac{v_{p,min}}{c\sigma^2}\right)^{-1}}_{(II)} \cdot \underbrace{\left(\frac{v_{p,q} - v_{p,min}}{v_{p,max} - v_{p,min}} - b\right)^2}_{(III)}, 1\right\}. \quad (8)$$

The influence function $H_2$ is accordingly used with high weight if in accordance with term I the environment of the voxel p is anisotropic, simultaneously in accordance with term II the minimum variance is small and accordance with term III the variance in the observed direction q lies in the vicinity of the minimum or of the maximum of the local variances, e.g. by the selection of b=½. The parameter c serves to adjust the dependency of the $CNR^2$ value $v_{p,min}/\sigma^2$, and a defines the size of the overall weight or of the maximum weight. With the weighting function selected in the equation (8) it is useful to optimize $H_2$ for the situation in which the pronounced tangential surfaces are present, and $H_1$ for the opposite case.

Also conceivable is a combination of the variants of equations (2) and (7). Embodiments of the method presented is not restricted to a specific number of dimensions and can be applied to 2D image or projection data, 3D image data or also 4D data, whereby as the third or fourth dimension the time can be included in dynamic images.

Figure 5:
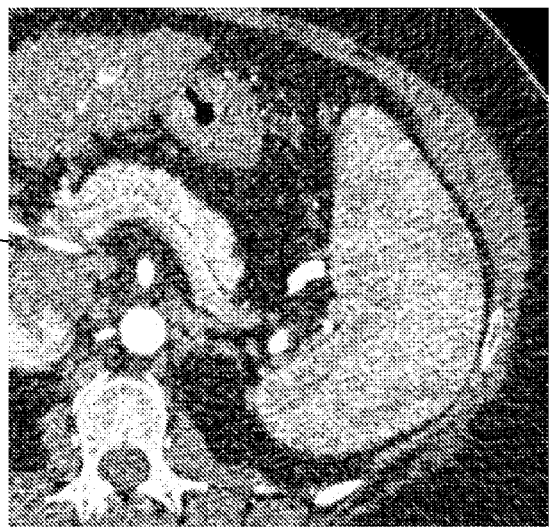
FIG. 5 shows an unfiltered CT image of a patient.
Figure 6:
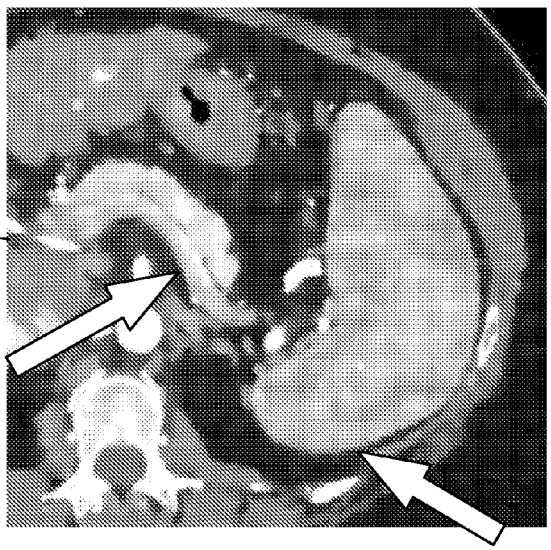
FIG. 6 shows a CT image from FIG. 5 with filtering according to the prior art.
Figure 7:
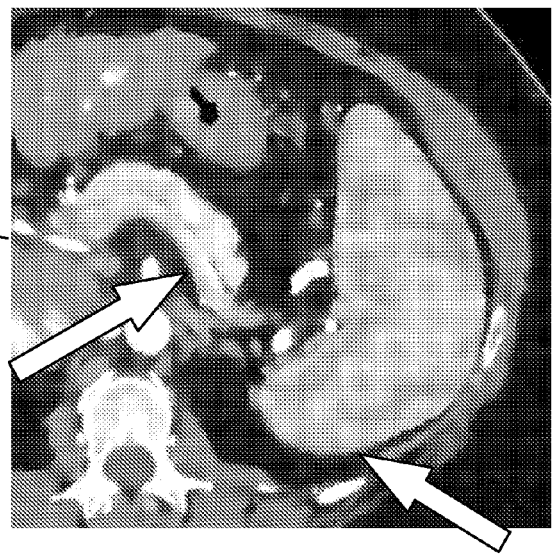
FIG. 7 shows a CT image from FIG. 5 with an embodiment of inventive filtering.

FIGS. 5 through 7 show an application example of the method in accordance with equation (7) for extreme filter strength. The initial diagram 3.1 in FIG. 5 in this case is initially filtered in accordance with equation (1) and has been shown with its result image 3.2 in FIG. 6. The H function in this case corresponds to the type from FIG. 4. The result of filtering in accordance with the inventive method is shown on diagram 3.3 in FIG. 7, where $H_1$ has been selected from a type in accordance with FIGS. 4 and $H_2$ from a type in accordance with FIG. 3. It is evident that in a few edges of the image in FIG. 6 the contours are defined with the original method by the form of the noise kernels, while in diagram 3.3 from FIG. 7, which was filtered with the inventively modified method, "unevennesses" in the size of the noise kernels in accordance with the tangential planes are removed on a larger length scale. The steepening effect of $H_2$ for large CNR values means that the edges in diagram 3.3 of FIG. 7 are however orthogonal to the tangential planes simultaneously sharper than in diagram 3.2 of FIG. 6. Salient points are marked with arrows in FIGS. 6 and 7.

Figure 8:
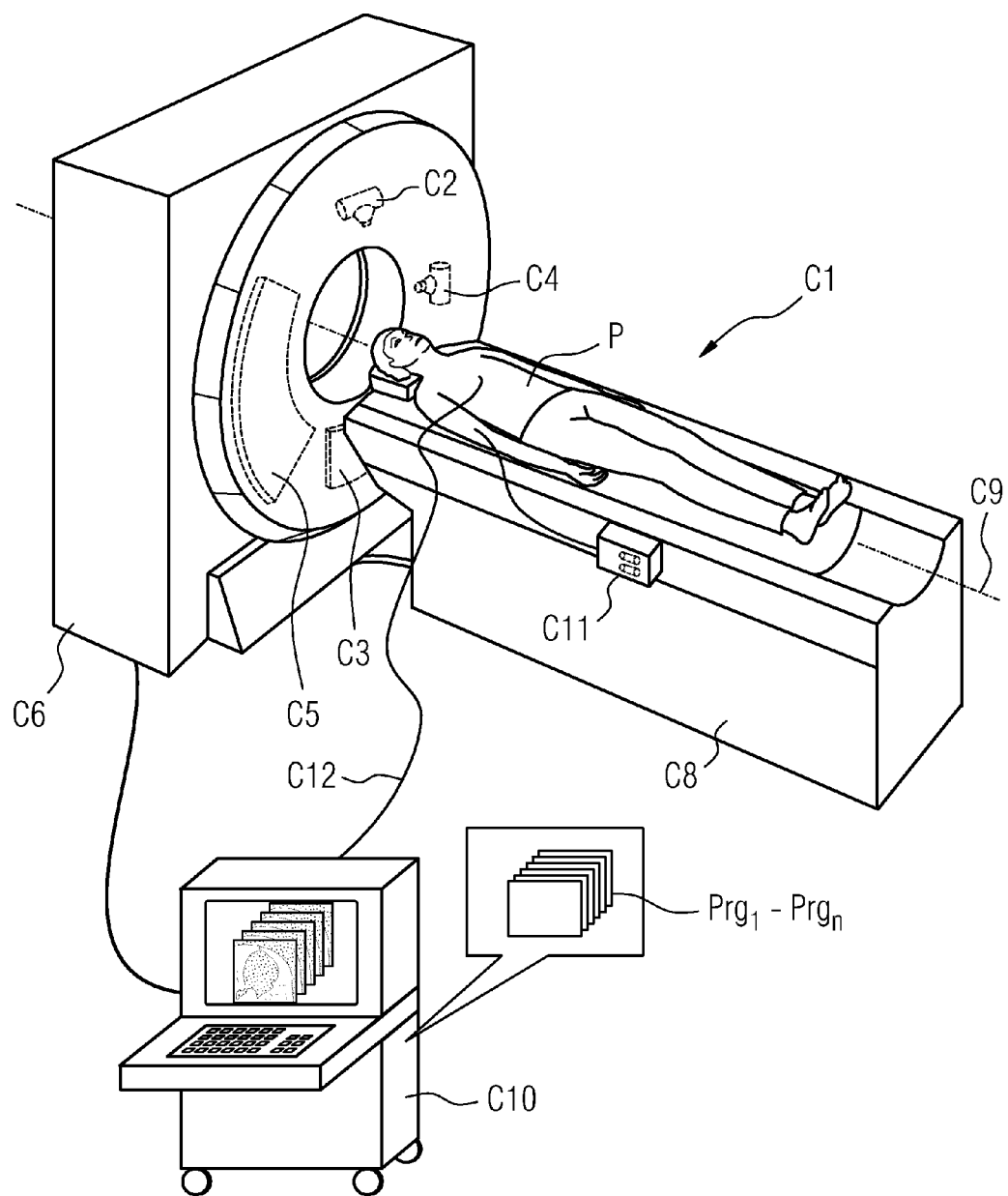
FIG. 8 shows a CT system with a computing unit for executing an embodiment of the inventive method and FIG. 9 shows a C-arm system with a computing unit for executing an embodiment of the inventive method.

FIG. 8 shows by way of example a CT system 1 in which an embodiment of the inventive method can be performed. The CT system C1 consists of a gantry housing C6 in which a first tube/detector system, consisting of a first X-ray tube C2 and an opposing first detector C3, are located on the gantry. Optionally a further tube/detector system can be provided consisting of the second X-ray tube C4 and the opposing second detector C5. Both tube/detector systems can rotate during the scanning around a field of view which is described here by an opening in the gantry housing C6, while a patient P who is located on a movable patient couch C8 is moved along a system axis C9 through the field of view. The movement of the patient P can in this case be undertaken both continuously and also sequentially. In addition, for an examination of a specific region, exclusively this specific region of the patient can also be brought into the field of view, at which it then remains stationary during the scan.

Control of the CT system 1 is assumed by a regulation and control unit C10 which has a memory with computer programs $Prg_1$ through $Prg_n$ in which the necessary methods for controlling the CT system and for evaluating the received detector data, including the reconstruction of corresponding image data, are stored. Embodiments of the inventive method can also be coded in a computer program and can be implemented in the program memory of the control and regulation unit C10, i.e. a computing unit, so that this method is executed during operation of the system in its method steps.

Figure 9:
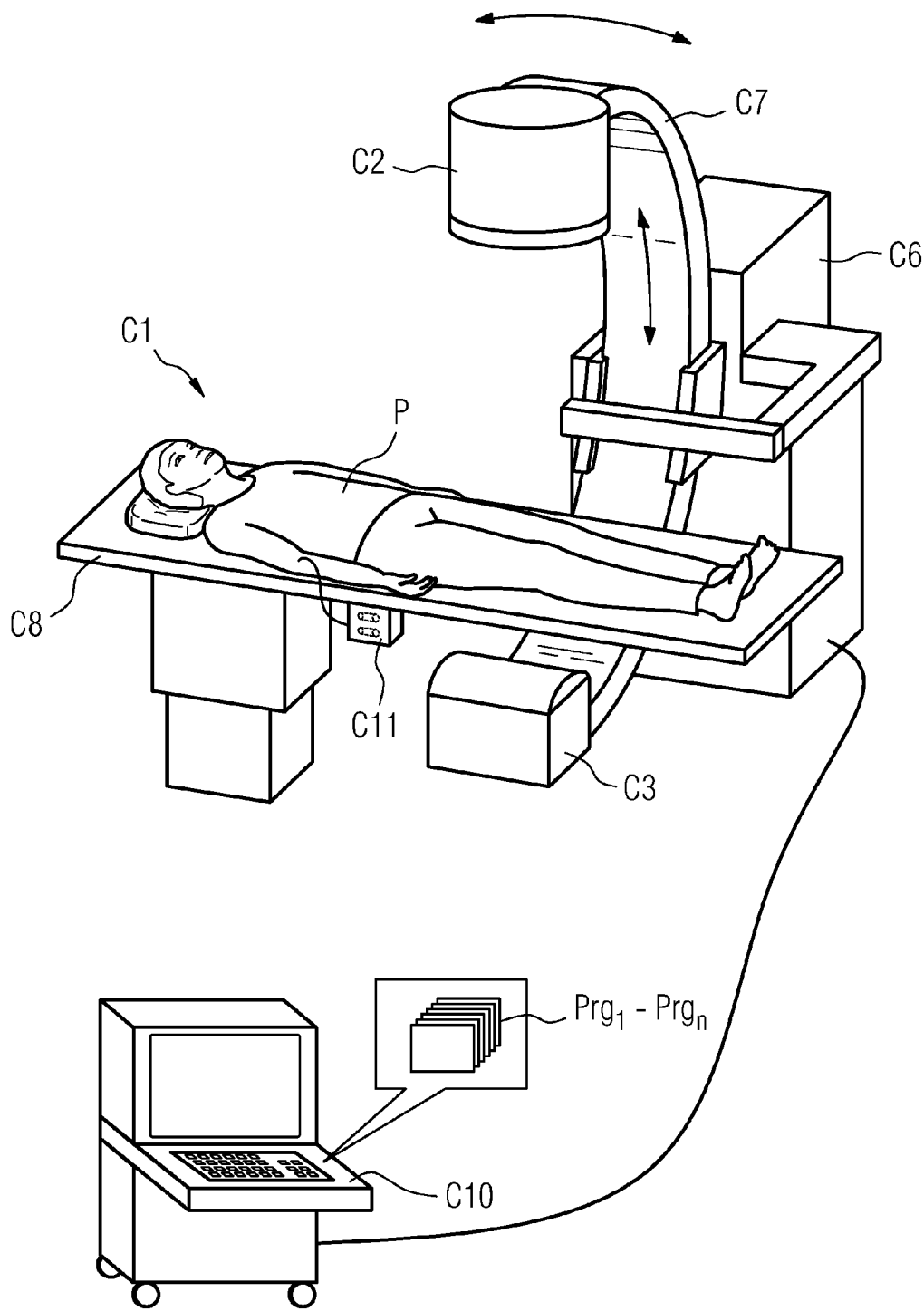

FIG. 9 likewise shows a CT system in the shape of a C-arm system C1 which has a C-arm C7 on the ends of which an X-ray tube C2 with an opposing detector C3 are located. This C-arm C7 can be moved with the aid of the drive system C6 in a rotational movement around a patient P who is located on a patient couch C8. As a result of the design of the C-arm system C1 the patient P is more easily accessible during the examination.

The regulation and control of the C-arm system C1 is undertaken by a regulation and control unit C10 comprising computer programs $Prg_1$ through $Prg_n$, wherein here too program code can be provided in the memory of this regulation and control unit which executes an embodiment of the inventive method during operation.

Overall, therefore, a method and an X-ray system, especially a CT system, are presented with the embodiments of the invention, wherein for reduction of the radiation dose used within the framework of an X-ray imaging examination for each pixel of a recorded image, structure information of a structure which may be present at a predetermined distance around the examined pixel is determined and a direction-dependent lowpass filter is applied to the respective examined pixel, which filter's spatial coverage is less than the predetermined distance and which takes into account the morphological information of a structure which may be present with a direction-dependent weighting of the lowpass filter.

The inventors have recognized the following: Morphological or structural filters mostly analyze the structural characteristics of the environment and especially detect the orientation of edges. This can be done with the aid of suitable operators, as are known from the prior art. As an alternative this can also be done by calculating direction-dependent variance values, as is shown in publications DE 10 2004 008 979 B4 and DE 10 2005 038 940 B4, the entire contents of each of which are hereby incorporated herein by reference. Subsequently locally adaptive filters are used which are adapted in the optimum manner in accordance with the orientation determined.

Since reliable analysis of the morphology requires a certain spatial coverage of the operators used, there is the danger of smaller structures being adversely affected during filtering. With a range that is too short the analysis is uncertain in the sense that statistical effects influence the computed orientation and thus the filtering undertaken does not match the actual orientation. To this extent, in accordance with the invention there should be a compromise in morphological filtering between the reliability of the orientation determination and the damage to small structures for which information from intelligent edge-preserving image filters which is either applied directly to image data for quality improvement or is used within the framework of iterative methods as a regularization step, can be used.

The result of the filtering and thus the potential for noise and dose reduction can thus be improved by both principles being skillfully combined. In this way it is possible to apply short-range and pixel value difference-dependent filters and orientation analyses to greater length scales simultaneously. A concrete example of this is described in detail further on in this document.

At least one embodiment of the invention thus shows a method and an X-ray system, especially a CT system, wherein for reduction of the radiation dose used within the framework of an X-ray imaging examination, for each pixel of a recorded image, structure information of a structure which may be present at a predetermined distance around the examined pixel is determined and a direction-dependent lowpass filter is applied to the respective pixel examined, which filter has a smaller spatial coverage than the predetermined distance and takes into account the morphological information of a structure that may be present with a direction-dependent weighting of the lowpass filter.

In accordance with this basic concept and the concrete example of an embodiment described further on in the document, the inventors propose to improve the known method for reduction of the radiation dose used within the framework of an imaging X-ray examination, especially of a CT examination, with the following method steps:

scanning or fluoroscopy of the patient by X-raying, generation of a projectional or tomographic image with a plurality of pixels, and filtering of the image for improving the image quality.

Inventively, at least one embodiment of this method is improved by:

structure information, including directional information of any structure which may be found, being sought for each pixel in a surrounding circle with a first radius around the examined pixel, and a direction-dependent lowpass filter being applied to the examined pixel, with on the one hand its spatial coverage being smaller than the first radius and on the other hand the direction information of any structure which may be found being taken into account for a direction-dependent weighting of the lowpass filter.

Advantageously the structure information can be determined by filtering with at least one morphological filter, as is known in the prior art.

Furthermore a diffusion filter can preferably be used as the direction-dependent lowpass filter.

In this case the diffusion filter can be realized for example by the iterative application of local filter steps.

In a first particular embodiment variant the local filter steps for a pixel value $V(p)$ can be defined at the position p as follows:

$$V'(p) = V(p) + \alpha \sum_q g_{q,p} \cdot (V(q) - V(p)) \cdot H\left(\frac{|V(q) - V(p)|}{\sigma}\right),$$

where:

q indexes the neighboring pixels of p, $g_{q,p}$ defines the filter coefficients in the position space and the influence function H determines the strength of the filtering depending on the local contrast-to-noise ratio (CNR), $|V(q)-V(p)|/\sigma$.

In a second particular embodiment variant the local filter steps for a pixel value $V(p)$ at position p can be defined with the following formula:

$$V'(p) = V(p) + \alpha \sum_q g_{q,p} \cdot (V(q) - V(p)) \cdot H\left(\frac{|V(q) - V(p)|}{\sigma} \cdot h(v_{p,q})\right),$$

where:

q indexes the neighboring pixels of p, $g_{q,p}$ defines the filter coefficients in the position space, the influence function H determines the strength of the filtering depending on the local contrast-to-noise ratio $|V(q)-V(p)|/\sigma$, with a local noise amplitude $\sigma$, and the correction factor $h(v_{p,q})$ is the characteristic that it is less than 1 for small variance values and greater than 1 for large variance values.

As an alternative the evaluation "small" or "large" in relation to the variance values can be undertaken by comparing a local one-dimensional variance $v_{p,q}$ in the direction of a connecting line of the pixels q and p with a local noise amplitude $\sigma$.

In accordance with a further variant of at least one embodiment, the evaluation "small" or "large" in relation to the variance values can be undertaken by comparing the variances of all directions, in that the minimum variance $v_{p,min}$ and maximum variance $v_{p,max}$ are determined in accordance with the rules:

$v_{p,min} = \min\{v_{p,q} | q \in \text{neighborhood of } p\}$ and $v_{p,max} = \max\{v_{p,q} | q \in \text{neighborhood of } p\}$, where under the condition $v_{p,q} \approx v_{p,min}$ a variance value is evaluated as "small" and
under the condition $v_{p,q} \approx v_{p,max}$ a variance value is evaluated as "large".

In addition the correction factor $h(v_{p,q})$ can be defined with $$h(v_{p,q}) = 1 + a \cdot \left(\frac{v_{p,q} - v_{p,min}}{v_{p,max} - v_{p,min}} - b\right),$$

where the parameter a defines the strength of the adaptation and the parameter b the position of the neutral point in the curve shape of the H function.

As an alternative the correction factor $h(v_{p,q})$ can also be computed with the equation $$h(v_{p,q}) = 1 + \alpha \cdot (1 - \eta_p) \cdot \left(\frac{v_{p,q} - v_{p,min}}{v_{p,max} - v_{p,min}} - b\right),$$

where:

the parameter a determines the strength of the adaptation,
the parameter b defines the position of the neutral point in the curve shape of the H function and
the correction factor $\eta_p$ is calculated with:

$$\eta_p = \frac{2 v_{p,min}}{v_{p,max} + v_{p,min}} \in ]0, 1].$$

$\eta_p$ represents a measure for the local isotropy, i.e. $\eta_p = 1$ for an isotropic environment (i.e. $v_{p,min} = v_{p,max}$) and $\eta_p \to 0$ for any given anisotropic environment (i.e. $v_{p,min} \ll v_{p,max}$).

Finally, in accordance with at least one embodiment of the invention, the local filter steps can also be computed for a pixel value $V(p)$ at the position p with:

$$V'(p) = V(p) + \alpha \sum_q g_{q,p} \cdot (V(q) - V(p)) \cdot \left[ (1 - c_{p,q}) \cdot H_1\left(\frac{|V(q) - V(p)|}{\sigma}\right) + c_{p,q} \cdot H_2\left(\frac{|V(q) - V(p)|}{\sigma}\right) \right],$$

where a convolution of two different influencing functions $H_1$ and $H_2$ is executed:

q indexes the neighboring pixels of p, $g_{q,p}$ defines the filter coefficients in the position space, the influence function H determines the strength of the filtering depending on the local contrast-to-noise ratio $|V(q)-V(p)|/\sigma$, with a local noise amplitude $\sigma$, and $c_{p,q}$ represents a weighting function or weighting factor.

In the last-mentioned variant of at least one embodiment of the inventive method $c_{p,q}$ the weighting function $c_{p,q}$ can be computed with the rule $$c_{p,q} = \min\left\{ a(1 - \eta_p)\left(1 + \frac{v_{p,min}}{c\sigma^2}\right)^{-1}\left(\frac{v_{p,q} - v_{p,min}}{v_{p,max} - v_{p,min}} - b\right)^2, 1 \right\},$$

where the following applies:
$\sigma^2$=local variance value (square of the local noise value)
c=scale parameter for definition of the adaptation strength to the local noise level.

In addition to embodiments of the inventive method, the inventors also disclose, in at least one embodiment, a computer system for processing X-ray and/or CT image datasets which comprises a memory and computer programs stored therein, wherein at least one computer program is to be stored and is to be executed during operation, and which performs a method with the following method steps:

receipt of X-ray or CT image datasets with a plurality of pixels, for each pixel structure information, including direction information of any structure which may be found, is searched for in a circular area with a first radius around the examined pixel, a direction-dependent lowpass filter is applied to the pixel under examination, wherein on the one hand its spatial coverage is less than the first radius and on the other hand the direction information of a structure which may possibly be found is taken into account for a direction-dependent weighting of the lowpass filter.

This inventive computer system of at least one embodiment can also include at least one computer program which executes the previously described method variants during operation.

It goes without saying that the features of the invention described hereintofore are not only able to be used in the combination specified in each case but also in other combinations or on their own, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, the method comprising:
   scanning or X-raying of a patient;
   generating a projectional or tomographic image with a plurality of pixels from the scan or x-ray of the patient, wherein, for each of the plurality of pixels, structure information, including direction information of a structure which may have been found, is searched for in a circular area with a first radius around an examined pixel; and
   generating a filtered image from the projectional or tomographic image by applying a direction-dependent lowpass filter to the examined pixels, wherein on the one hand its spatial coverage is less than a first radius and on the other hand the direction information of a structure which may have been found is taken into account for a direction-dependent weighting of the lowpass filter.

2. The method as claimed in claim 1, wherein the structure information is determined by filtering with at least one morphological filter.

3. The method as claimed in claim 2, wherein a diffusion filter is used as the direction-dependent lowpass filter.

4. The method as claimed in claim 3, wherein the diffusion filter is realized by the iterative application of local filter steps.

5. The method as claimed in claim 4, wherein the local filter steps are defined for a pixel value V(p) at the position p as follows:

$$V'(p) = V(p) + \alpha \sum_q g_{q,p} \cdot (V(q) - V(p)) \cdot H\left(\frac{|V(q) - V(p)|}{\sigma}\right),$$

where:
   q indexes the neighboring pixels of p,
   $g_{q,p}$ defines the filter coefficients in the position space and the influence function H determines the strength of the filtering depending on the local contrast-to-noise ratio (CNR), $|V(q)-V(p)|/\sigma$.

6. The method as claimed in claim 4, wherein the local filter steps are defined for a pixel value V(p) at the position p as follows:

$$V'(p) = V(p) + \alpha \sum_q g_{q,p} \cdot (V(q) - V(p)) \cdot H\left(\frac{|V(q) - V(p)|}{\sigma} \cdot h(v_{p,q})\right),$$

where:
   q indexes the neighboring pixels of p,
   $g_{q,p}$ defines the filter coefficients in the position space,
   the influence function H determines the strength of the filtering depending on the local contrast-to-noise ratio $|V(q)-V(p)|/\sigma$, with a local noise amplitude $\sigma$, and
   the correction factor $h(v_{p,q})$ possesses the characteristic that it is less than 1 for small variance values and is greater than 1 for large variance values.

7. A non-transitory computer-readable storage medium including program segments for, when executed on a computer device, causing the computer device to implement the method of claim 2.

8. The method as claimed in claim 1, wherein a diffusion filter is used as the direction-dependent lowpass filter.

9. The method as claimed in claim 8, wherein the diffusion filter is realized by the iterative application of local filter steps.

10. The method as claimed in claim 9, wherein the local filter steps are defined for a pixel value V(p) at the position p as follows:

$$V'(p) = V(p) + \alpha \sum_q g_{q,p} \cdot (V(q) - V(p)) \cdot H\left(\frac{|V(q) - V(p)|}{\sigma} \cdot h(v_{p,q})\right),$$

where:
   q indexes the neighboring pixels of p,
   $g_{q,p}$ defines the filter coefficients in the position space and the influence function H determines the strength of the filtering depending on the local contrast-to-noise ratio (CNR), $|V(q)-V(p)|/\sigma$.

11. The method as claimed in claim 9, wherein the local filter steps are defined for a pixel value V(p) at the position p as follows:

$$V'(p) = V(p) + \alpha \sum_q g_{q,p} \cdot (V(q) - V(p)) \cdot H\left(\frac{|V(q) - V(p)|}{\sigma}\right),$$

where:
   q indexes the neighboring pixels of p,
   $g_{q,p}$ defines the filter coefficients in the position space,
   the influence function H determines the strength of the filtering depending on the local contrast-to-noise ratio $|V(q)-V(p)|/\sigma$, with a local noise amplitude $\sigma$, and
   the correction factor $h(v_{p,q})$ possesses the characteristic that it is less than 1 for relatively small variance values and is greater than 1 for relatively large variance values.

12. The method as claimed in claim 11, wherein the relative assessment of small or large in relation to the variance values is undertaken by comparing a local one-dimensional variance $v_{p,q}$ in the direction of a connecting line of the pixels q and p with a local noise amplitude $\sigma$.

13. The method as claimed in claim 11, wherein, the relative assessment of small or large in relation to the variance values is undertaken by comparing the variances of all directions in that the minimum variance $v_{p,min}$ and maximum variance $v_{p,max}$ are determined in accordance with the rules:
   $v_{p,min} = \min\{v_{p,q}|q \in \text{neighborhood of } p\}$ and
   $v_{p,max} = \max\{v_{p,q}|q \in \text{neighborhood of } p\}$
   where
      under the condition $v_{p,q} \approx v_{p,min}$ a variance value is evaluated as "small" and under the condition $v_{p,q} \approx v_{p,max}$ a variance value is evaluated as "large".

14. The method as claimed in claim 11, wherein the correction factor $h(v_{p,q})$ is defined with:

$$h(v_{p,q}) = 1 + a \cdot \left(\frac{v_{p,q} - v_{p,min}}{v_{p,max} - v_{p,min}} - b\right),$$

where the parameter a determines the strength of the adaptation and the parameter b defines the position of the neutral point in the curve shape of the H function.

15. The method as claimed in claim 11, wherein the correction factor $h(v_{p,q})$ is defined with:

$$h(v_{p,q}) = 1 + a \cdot (1 - \eta_p) \cdot \left( \frac{v_{p,q} - v_{p,min}}{v_{p,max} - v_{p,min}} - b \right),$$

where:
the parameter a determines the strength of the adaptation,
the parameter b defines the position of the neutral point in the curve shape of the H function and
the correction factor $\eta_p$ is calculated with:

$$\eta_p = \frac{2v_{p,min}}{v_{p,max} + v_{p,min}} \in ]0, 1].$$

16. The method as claimed in claim 9, wherein the local filter steps for a pixel value V(p) at the position p are defined as follows:

$$V'(p) = V(p) + \alpha \sum_q g_{q,p} \cdot (V(q) - V(p)) \cdot \begin{bmatrix} (1 - c_{p,q}) \cdot H_1\left(\frac{|V(q) - V(p)|}{\sigma}\right) + \\ c_{p,q} \cdot H_2\left(\frac{|V(q) - V(p)|}{\sigma}\right) \end{bmatrix}$$

where a convolution of two different influence functions $H_1$ and $H_2$ is executed and:
q indexes the neighboring pixels of p,
$g_{q,p}$ defines the filter coefficients in the position space,
the influence function H determines the strength of the filtering depending on the local contrast-to-noise ratio $|V(q)-V(p)|/\sigma$, with a local noise amplitude $\sigma$, and
$c_{p,q}$ represents a weighting function or weighting factor.

17. The method as claimed in claim 16, wherein $c_{p,q}$ the weighting function $c_{p,q}$ is computed with:

$$c_{p,q} = \min\left\{ a(1 - \eta_p)\left(1 + \frac{v_{p,min}}{c\sigma^2}\right)^{-1}\left(\frac{v_{p,q} - v_{p,min}}{v_{p,max} - v_{p,min}} - b\right)^2, 1 \right\}.$$

18. A non-transitory computer-readable storage medium including program segments for, when executed on a computer device, causing the computer device to implement the method of claim 1.

19. The method as claimed in claim 1, wherein the method is for reduction of the radiation dose used within the framework of an X-ray imaging examination.

20. A computer system for processing at least one of X-ray and CT image datasets comprising:
a memory, including computer programs stored therein, at least one computer program, when executed during operation, causes computer system to perform at least the following:
receiving X-ray or CT image datasets with a plurality of pixels;
searching, for each of the plurality of pixels, for structure information including direction information of any structure which may be found is searched for in a circular area with a first radius around an examined pixel; and
generating a filtered image from the X-ray or CT image datasets by applying a direction-dependent lowpass filter to the examined pixels, wherein on the one hand its spatial coverage is less than a first radius and on the other hand the direction information of a structure which may possibly be found is taken into account for a direction-dependent weighting of the lowpass filter.

* * * * *